United States Patent
Bow et al.

(10) Patent No.: US 10,271,935 B2
(45) Date of Patent: Apr. 30, 2019

(54) UNIT DOSE PACKAGE WITH BALL SEAL

(71) Applicant: Team Technologies, Inc., Morristown, TN (US)

(72) Inventors: Clark F. Bow, Dandridge, TN (US); Mitchell J. Wagner, Sugar Grove, IL (US)

(73) Assignee: Team Technologies, Inc., Morristown, TN (US)

( * ) Notice: Subject to any disclaimer, the term of this patent is extended or adjusted under 35 U.S.C. 154(b) by 116 days.

(21) Appl. No.: 15/399,421

(22) Filed: Jan. 5, 2017

(65) Prior Publication Data

US 2017/0209249 A1    Jul. 27, 2017

Related U.S. Application Data

(60) Provisional application No. 62/286,563, filed on Jan. 25, 2016.

(51) Int. Cl.
| | |
|---|---|
| *A61C 17/02* | (2006.01) |
| *A61C 19/06* | (2006.01) |
| *A61M 35/00* | (2006.01) |
| *A61C 19/04* | (2006.01) |
| *A46B 1/00* | (2006.01) |
| *A46B 9/02* | (2006.01) |
| *A46B 11/00* | (2006.01) |

(52) U.S. Cl.
CPC .............. *A61C 19/066* (2013.01); *A46B 1/00* (2013.01); *A46B 9/021* (2013.01); *A46B 11/0003* (2013.01); *A61C 19/04* (2013.01); *A61M 35/003* (2013.01)

(58) Field of Classification Search
CPC .... A61C 19/066; A61C 19/04; A61M 35/003; A61M 39/28; A61M 39/24; A61M 39/02; A61M 39/26; A45D 40/06; A45D 40/20; A46B 1/00; A46B 9/021; A46B 11/0003; B67C 7/00; B65D 1/323; B65D 1/0223; B65D 25/38; B65D 43/02; B65D 47/283
See application file for complete search history.

(56) References Cited

U.S. PATENT DOCUMENTS

| | | | |
|---|---|---|---|
| 1,283,050 A * | 10/1918 | Berg | ...................... B65D 35/40 222/207 |
| 3,245,587 A | 4/1966 | Brown | |
| 4,245,635 A * | 1/1981 | Kontos | ................. A61M 39/06 251/149.1 |
| 4,370,989 A * | 2/1983 | Taylor | ................. A45D 34/042 132/317 |
| 4,588,319 A | 5/1986 | Niemeyer | |

(Continued)

*Primary Examiner* — Nicholas D Lucchesi
(74) *Attorney, Agent, or Firm* — Luedeka Neely Group, P.C.

(57) ABSTRACT

A single use fluid delivery system including a fluid containing vial fitted with a non-removable sealing plug; a separate fluid applicator non-removably installable on the fluid vial; and a ball seal structure located on the fluid vial and configured to seal the fluid vial until the applicator is installed. The fluid filled and sealed vial and the applicator are provided as separate pieces, and during use of the single dose fluid delivery system the applicator is installed onto the vial, and during installation of the applicator onto the vial, the seal is dislodged and opens a channel for the fluid to flow to the applicator.

18 Claims, 9 Drawing Sheets

(56) References Cited

U.S. PATENT DOCUMENTS

| | | | | |
|---|---|---|---|---|
| 4,703,781 A | * | 11/1987 | Meyer | B65B 3/003 141/11 |
| 5,139,654 A | * | 8/1992 | Carpenter | E21B 49/081 210/136 |
| 5,217,433 A | * | 6/1993 | Bunin | A61J 1/2093 206/221 |
| 5,397,314 A | * | 3/1995 | Farley | A61B 17/3498 137/527.6 |
| 5,423,791 A | * | 6/1995 | Bartlett | A61J 1/2096 604/403 |
| 5,520,665 A | * | 5/1996 | Fleetwood | A61M 39/26 604/246 |
| 5,850,908 A | * | 12/1998 | Jasek | B65D 47/283 220/203.23 |
| 6,293,721 B1 | * | 9/2001 | Bow | A45D 40/02 401/78 |
| 6,537,260 B1 | * | 3/2003 | Lamb | A61M 3/0262 604/279 |
| 7,207,967 B1 | * | 4/2007 | Bellhouse | A61M 5/3015 604/68 |
| 8,449,213 B2 | | 5/2013 | Chang | |
| 9,932,139 B2 | * | 4/2018 | Scott | B65D 1/323 |
| 2002/0179179 A1 | * | 12/2002 | Volpenheim | B65D 35/40 141/381 |
| 2004/0068222 A1 | * | 4/2004 | Brian | A61M 11/06 604/65 |
| 2004/0097890 A1 | * | 5/2004 | Wilkinson | A61M 35/003 604/289 |
| 2005/0087715 A1 | * | 4/2005 | Doyle | A61M 39/045 251/149.1 |
| 2005/0209554 A1 | * | 9/2005 | Landau | A61M 5/30 604/72 |
| 2010/0044375 A1 | * | 2/2010 | Rockstad | B65D 1/323 220/203.29 |
| 2011/0208128 A1 | * | 8/2011 | Wu | A61J 1/2096 604/247 |
| 2012/0059314 A1 | * | 3/2012 | Eichhorst | A61M 5/204 604/68 |
| 2012/0070220 A1 | | 3/2012 | Ruiz, Sr. | |
| 2016/0167826 A1 | * | 6/2016 | Scott | B65D 47/283 222/182 |
| 2018/0239370 A1 | * | 8/2018 | Perry, Jr. | G05D 7/0133 |

* cited by examiner

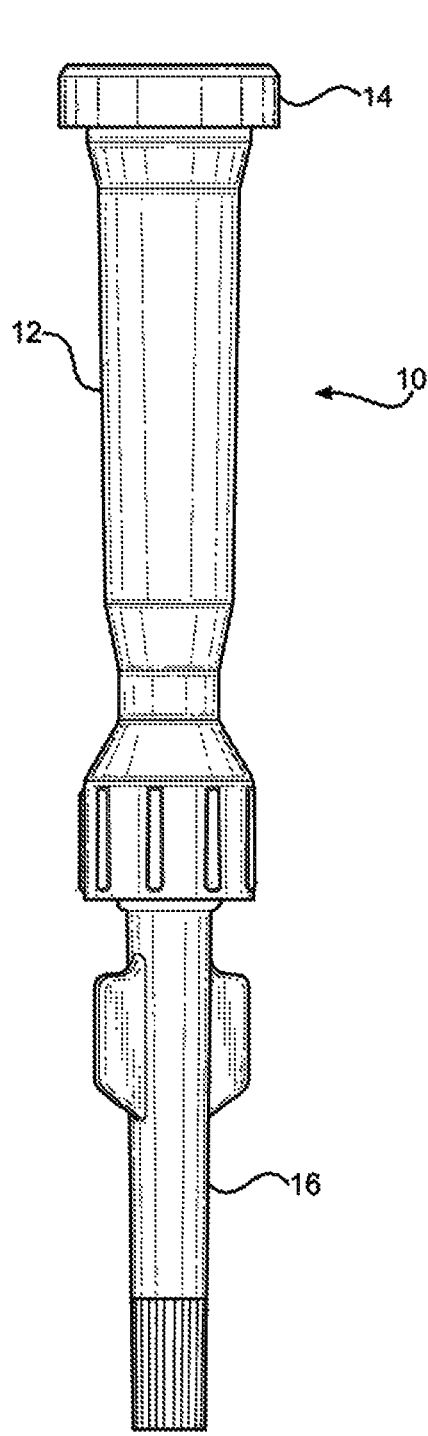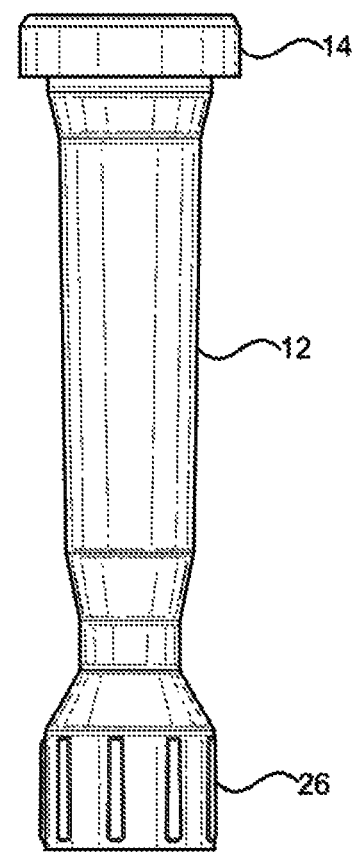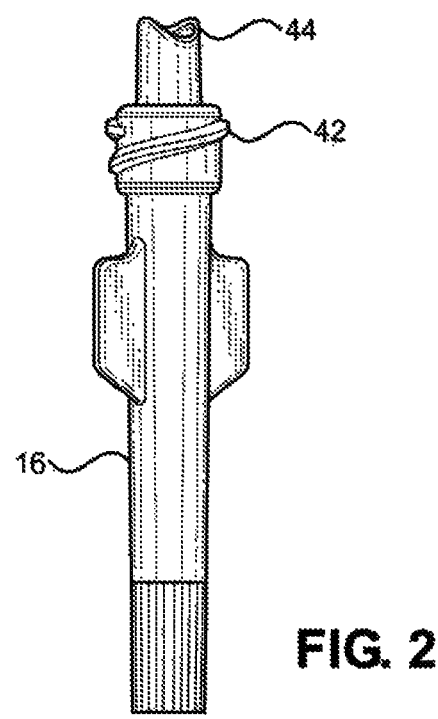
FIG. 1  FIG. 2

UNIT DOSE PACKAGE WITH BALL SEAL

FIELD

This disclosure relates to the field of unit dose fluid applicators. More particularly, this disclosure relates to a single-use fluid applicator configured for applying dental fluids.

BACKGROUND

Improvement is desired in the provision of single use fluid application packages of the type having a brush for applying a fluid. In particular, improvement is desired in the field of dental fluid application packages.

What is desired is a package that is relatively thin so as to be easily grasped and manipulated by a dentist when working inside a mouth of a patient, and which reliably and accurately applies dental fluids such as dental varnish. It is also desired that the fluid is secure until ready for use, and that the application cannot be readily resealed so as to be reusable. That is, the application package is specifically configured for single use.

The disclosure advantageously provides a single use fluid delivery system. In particular, the delivery system is configured for use to apply a single dose of dental treatment fluids. However, fluid delivery systems according to the disclosure may be utilized to deliver a variety of fluids for various uses.

SUMMARY

The disclosure relates to single use fluid delivery system.

In one aspect, the system includes a fluid containing vial fitted with a non-removable sealing plug; a separate fluid applicator non-removably installable on the fluid vial; and a ball seal structure located on the fluid vial and configured to seal the fluid vial until the applicator is installed.

The fluid filled and sealed vial and the applicator are provided as separate pieces, and during use of the single dose fluid delivery system the applicator is installed onto the vial, and during installation of the applicator onto the vial, the seal provided by the ball is dislodged and opens a channel for the fluid to flow to the applicator.

In another aspect, the system includes a vial containing a fluid and the vial being formed to be squeezable under hand pressure for dispensing of fluid from the vial. The vial has one end including a non-removable sealing plug and an opposite end having a ball seal structure configured to seal the fluid vial and including a ball.

The system also includes a separate fluid applicator non-removably installable onto the fluid vial, the applicator having an inlet that cooperates with the ball of the ball seal structure to dislodge the ball during installation of the applicator onto the vial to enable fluid to travel from the vial to the applicator after installation of the applicator onto the vial. The inlet is configured to cooperate with the ball after installation of the applicator onto the vial such that the ball does not block the travel of fluid from the vial to the applicator.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIG. 1 shows an assembled fluid applicator according to the disclosure.

FIG. 2 is a partially exploded view of the fluid applicator of FIG. 1.

DETAILED DESCRIPTION

Figure 3:
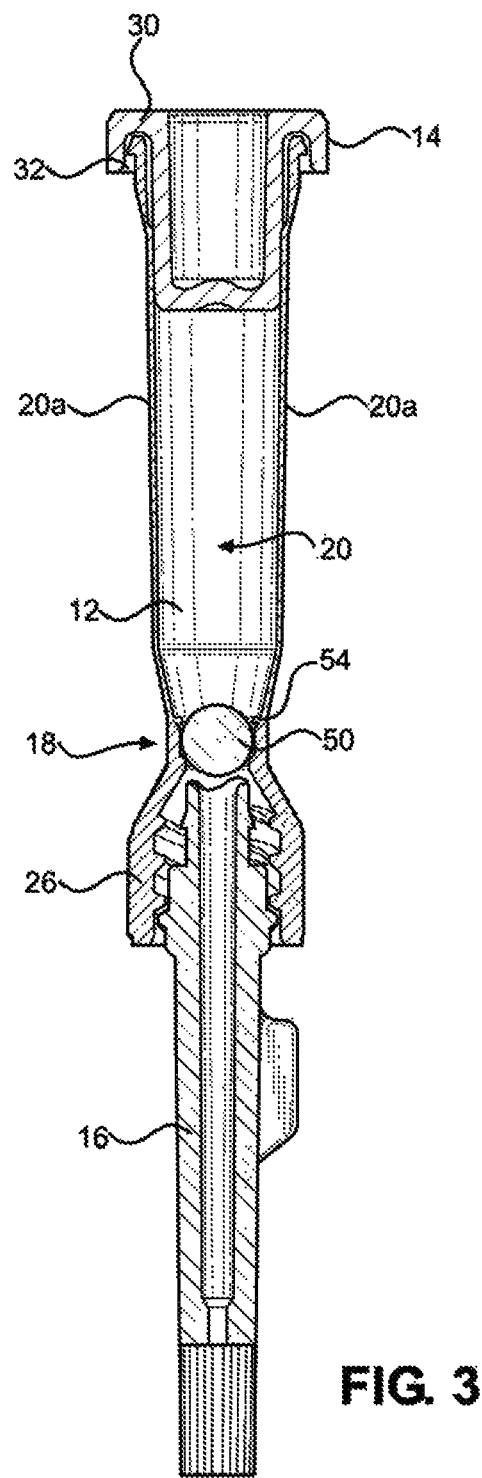
FIG. 3 is a cross-sectional view of the assembled fluid applicator of FIG. 1.

With reference to the drawings, there is shown a single use or single dose fluid delivery system 10. The delivery system 10 includes a fluid vial 12 fitted with a non-removable sealing plug 14. A separate fluid applicator 16 is non-removably installable on the fluid vial 12. The delivery system 10 also includes a ball seal structure 18 that seals the fluid vial 12 until the applicator 16 is installed.

The fluid vial 12 may be of molded plastic construction and provides an interior reservoir 20 that will be supplied to the end user pre-filled with a desired amount of a fluid. The reservoir 20 preferably includes relatively thin sidewall 20a that enable a user to squeeze the reservoir 20 using hand pressure to urge the fluid toward the applicator 16 during use of the delivery system 10 for delivery of the fluid for its intended use.

In one embodiment, the fluid is dental varnish in an amount sufficient to complete one dental varnish procedure. In other embodiments, the fluid may be other dental treatment fluids such as tooth whitening fluid or gel. The fluid may also be nail polish, nail polish remover, rubbing alcohol, topical antiseptic/anesthetic, cold sore treatment, wart remover, adhesives, and other fluids for treatment of a body part or other workpiece. The vial 12 is generally cylindrical and dimensioned so as to be easily grasped and manipulated by a user. In one embodiment, the vial may be about 0.25 to 0.5 inches in diameter.

An upper end of the reservoir 20 provides an opening 22 configured to cooperate with the sealing plug 14. A lower end of the reservoir 20 tapers to a seal section 24. The seal section 24 then enlarges to provide a docking port 26. The docking port 26 includes internal threads 28. The vial 12 provides a continuous fluid flow path from the opening 22 to the docking port 26.

The sealing plug 14 may be of molded plastic construction and is configured as a one-way snap-on cap for sealing the vial 12 after the vial 12 has been filled with a desired amount of fluid. The opening 22 of the vial 12 may include an enlarged rim 30, and the plug 14 includes rim locks 32 that lock to the rim 30 once the plug 14 has been installed. If the plug 14 is thereafter forcibly removed from the vial 12, the rim locks 32 or the rim 30 or both will be damaged in the process so that the plug 14 is no longer suitable for sealing the vial 12. This helps prevent against refilling and reuse of the delivery system 10.

The applicator 16 as shown is of one-piece molded plastic construction. In one embodiment, the applicator 16 is formed from a low-density polyethylene to provide sufficient softness to integrally molded bristles. Other plastics, such as medium-density polyethylene, may be used in other embodiments, especially embodiments where integrally molded bristles are not used. In other embodiments, the applicator 16 includes harder plastics for some portions and softer plastics for patient contact portions. The applicator 16 provides an elongate wand structure that facilitates application of fluid.

A distal end of the applicator 16 terminates in a soft fluid application structure, such as a brush 40. A proximal end of the applicator 16 includes threads 42 to cooperate with the threads 28 of the docking port 26 of the vial 12.

In a preferred embodiment, the distal end of the applicator 16 has an outside diameter of 0.1-0.3 inches. As noted above, the brush 40 is preferably formed from plastic bristles molded unitarily as part of the applicator 16 extending from the distal end of the applicator 16. In other embodiments, the bristles may be attached to a tip end of the applicator such as by use of a staple. In one preferred embodiment, there are three concentric rings of bristles, although in other embodiments there may be two to six concentric rings of bristles. The outside ring preferably includes 20-30 triangular bristles with a width at the bristle root of about 0.01-0.04 inches, as it has been determined that a smaller number of thinner bristles is difficult to mold consistently and a larger number of thicker bristles were stiffer than preferred for proper fluid application. In alternate embodiments, the bristles may be four-sided or have other cross sections. In preferred embodiments, the bristles have a length of about 0.2-0.7 inches.

In other embodiments, the distal end of the applicator 16 terminates in other application structures, such as a flocked tip, foam pad, or cotton swab, or the distal end may terminate simply as the tip end having an outlet in flow communication with the reservoir 20, which provides a fluid application structure.

The proximal end of the applicator 16 also includes an inlet 44 that cooperates with the vial 12 to provide a fluid tight connection for the assembled delivery system 10. For example, the inlet 44 may increase in diameter from the fee end to provide a taper that engages a similar taper on the interior of the vial 12 to provide a tight interference fit as the applicator 16 is threaded onto the vial 12. Fins 46 are desirably located on the applicator 16 for finger leverage for threadably installing the applicator 16 onto the vial 12. A locking feature, such as one or more detents 48, is desirably formed on the inlet 44 so that the applicator 16 clicks into place on the vial 12 at the end of the screw thread travel to make it harder for the user to remove the applicator 16 after it is assembled onto the vial 12. The applicator 16 provides a continuous fluid flow path from the proximal end to the distal end for fluid to travel therethrough for delivery via the brush 40. The fluid flow path is preferably substantially cylindrical with a diameter of 0.04-0.2 inches, most preferably about 0.1 inches.

Figure 4:
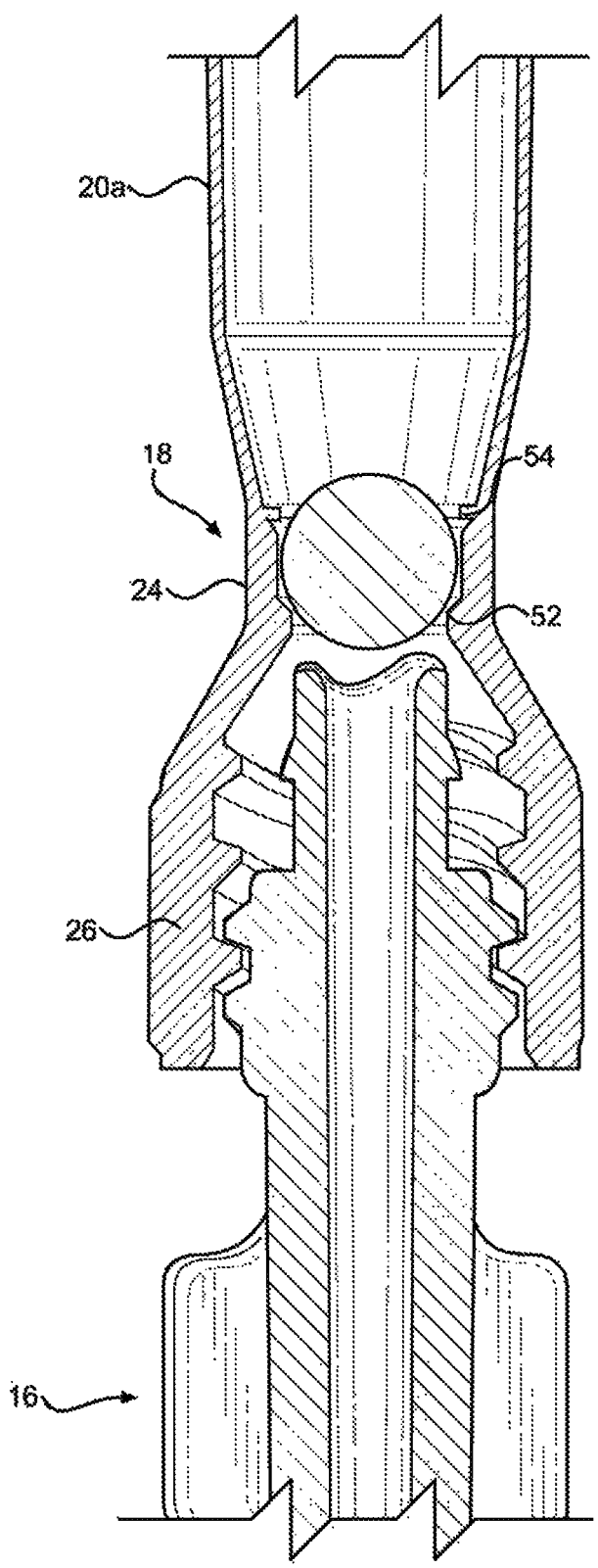
FIGS. 4 and 5 depict aspects of the assembly of the fluid applicator of FIG. 1, in which a ball seal component of the fluid applicator is disabled upon assembly.

With reference to FIG. 4, the ball seal structure 18 includes a ball 50, preferably a high-density polyethylene ball used as a plug to cooperate with and seal the seal section 24 of the lower end of the vial 12. In other embodiments, the ball 50 may be formed from other plastics or metal materials. The ball 50 is preferably 0.1-0.3 inches in diameter, and most preferably 3/16 inches in diameter. The ball 50 seals the vial 12 until the applicator 16 is installed on the vial 12. In this regard, the seal section 24 of the vial 12 is a narrow tubular section configured to snugly engage the ball 50 prior to assembly of the applicator 16 onto the vial 12. The seal section 24 includes a reduced diameter throat 52 so that when the ball 50 is located in the seal section 24 during manufacture the throat 52, the ball 50 is positioned to cooperate with the vial 12 when it is filled with fluid to provide a fluid tight seal. An upper retaining ring 54 of the seal section 24 also cooperates with the ball 50 to retain it in place in the seal section 24 and urge the ball 50 against the throat 52.

Figure 5:
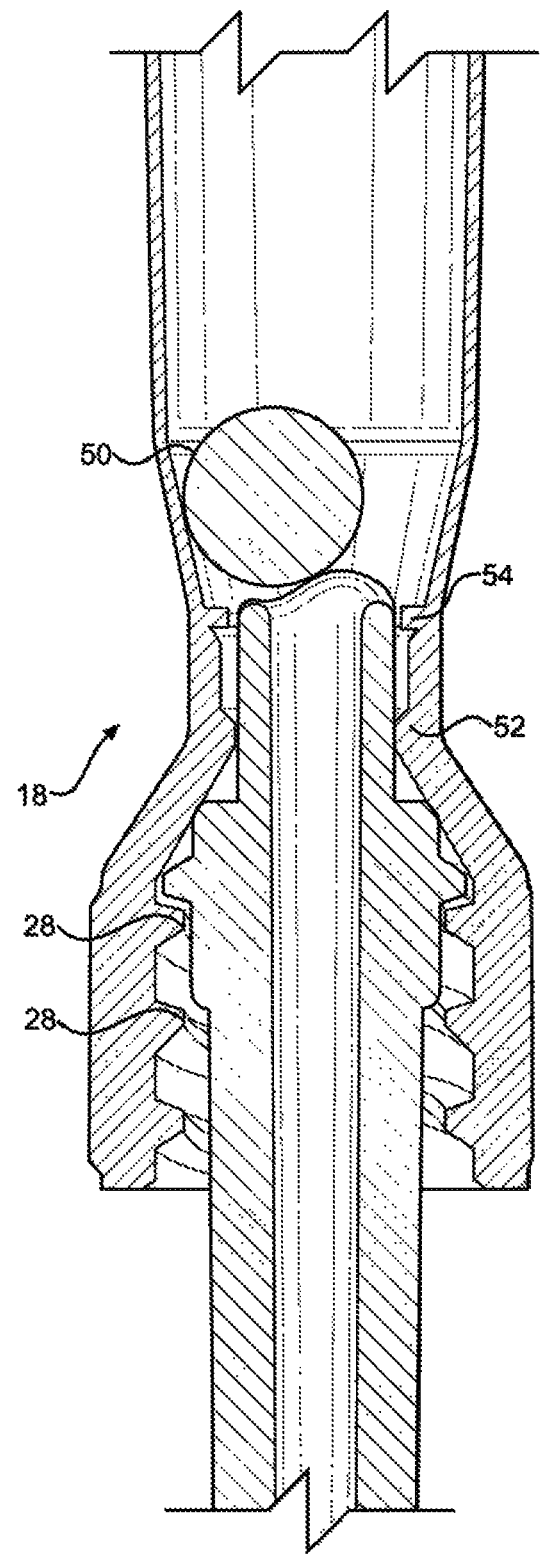
Figure 6:
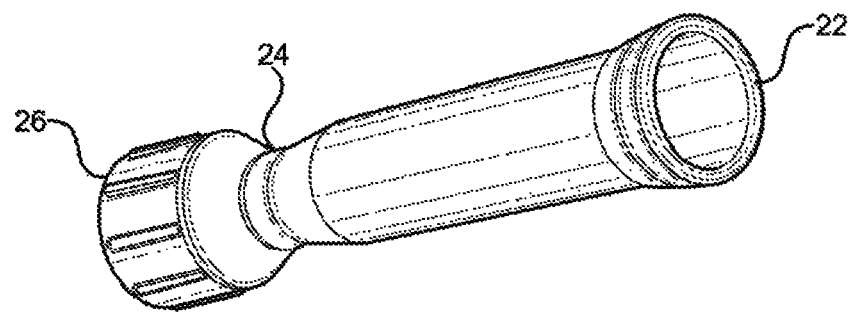
FIGS. 6, 7, and 8 show a fluid vial component of the fluid applicator of FIG. 1.
Figure 7:
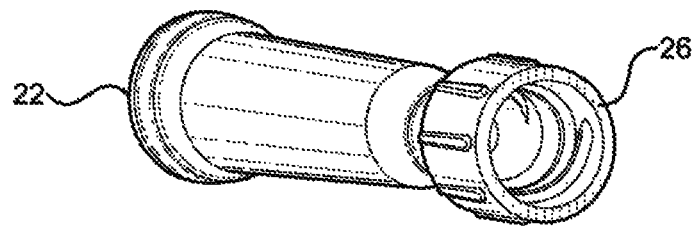
Figure 8:
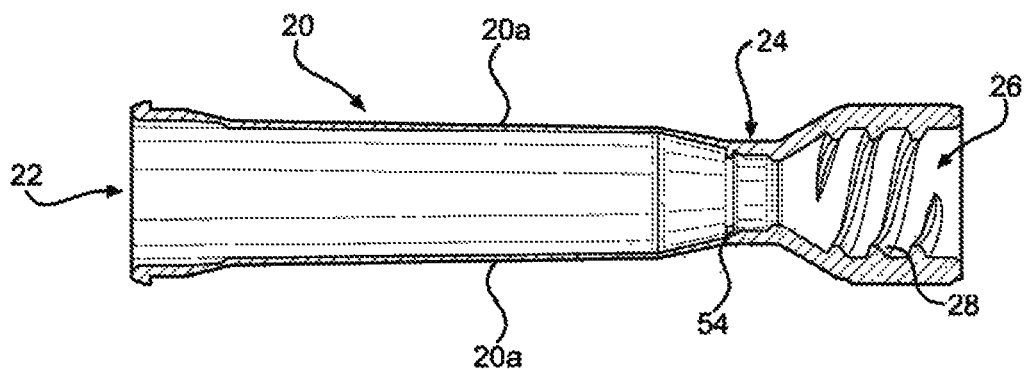
Figure 9:
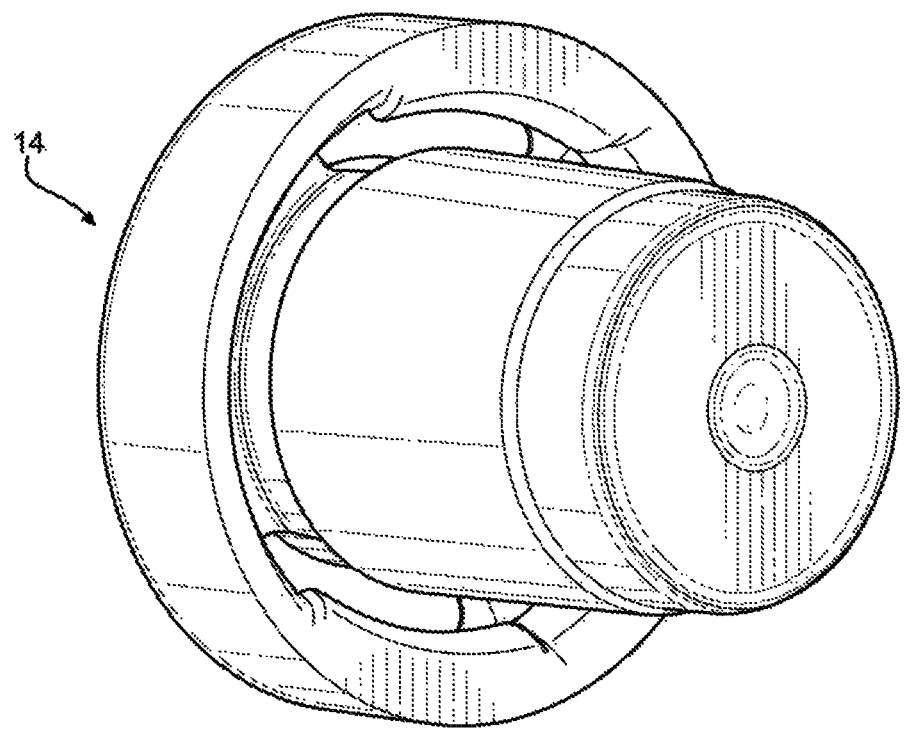
FIGS. 9 and 10 show a plug component of the fluid applicator of FIG. 1.
Figure 10:
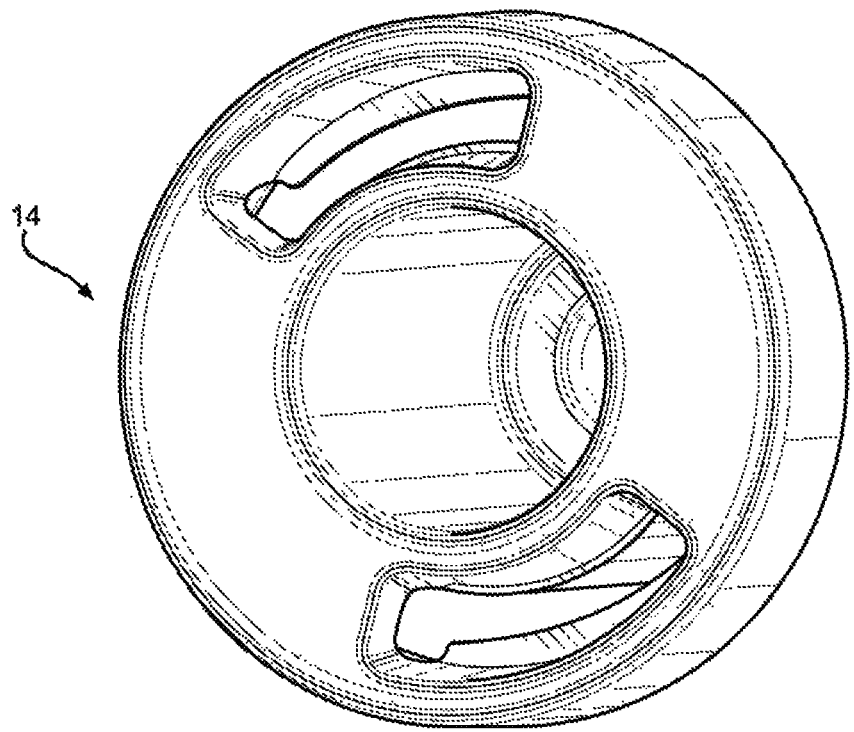
Figure 11:
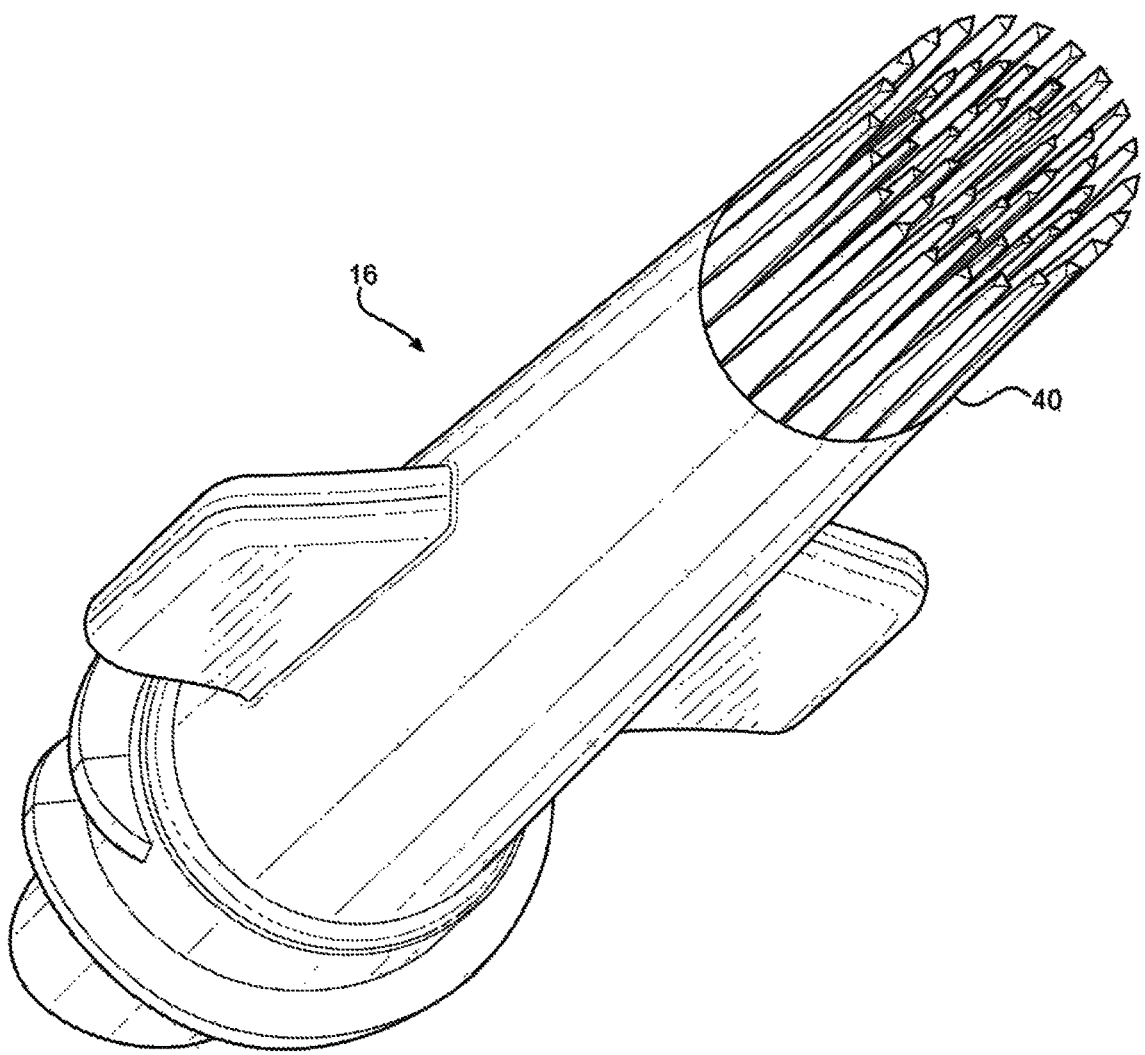
FIGS. 11, 12, 13, and 14 show an applicator brush component of the fluid applicator of FIG. 1.
Figure 12:
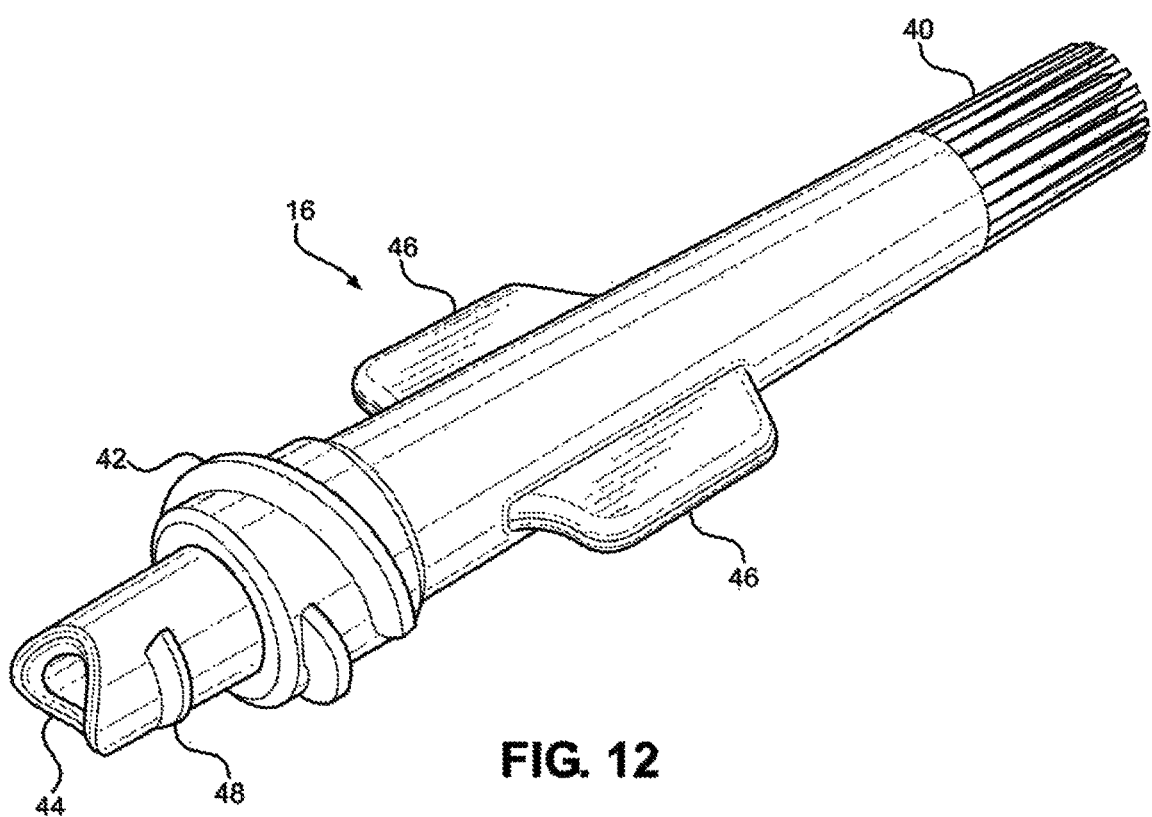
Figure 13:
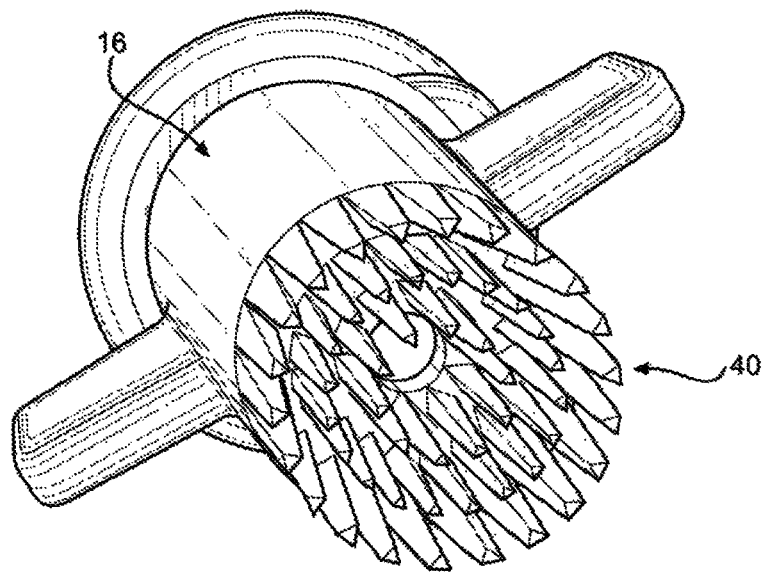
Figure 14:
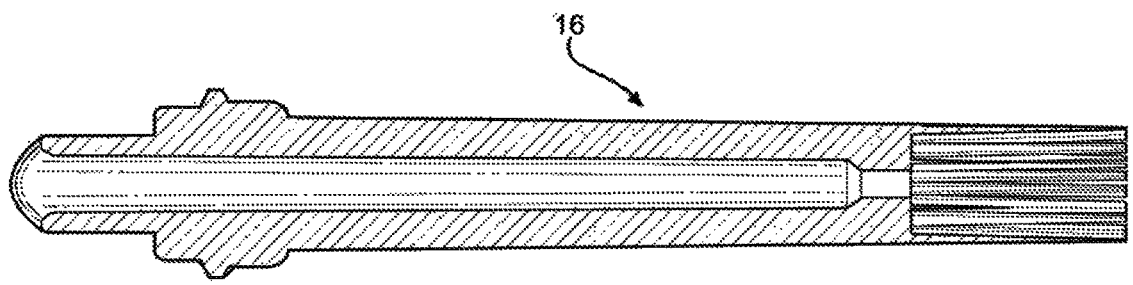

Turning to FIG. 5, when the applicator 16 is installed onto the vial 12, the ball 50 is dislodged to break the seal provided by the ball 50 to permit fluid to flow from the vial 12 to the applicator 16. The ball 50 is dislodged by travel of the inlet 44 of the applicator 16 into the and past the seal section 24 of the vial 12. As this occurs, the detents 48 click into place on the vial 12 at the end of the screw thread travel to make it harder for the user to remove the applicator 16 after it is assembled onto the vial 12. The end of the inlet should be sufficiently sized to dislodge the ball 50, preferably 0.1-0.3 inches in diameter. The end of the inlet 44 is also advantageously formed so that as the ball 50 rests against the inlet 44, the ball 50 cannot block or seal against the flow of fluid into the inlet 44. As shown, the inlet 44 has a sinusoidal curvature so that the ball 50 can only touch a portion of the inlet 44 at any time. The ball 50 also remains present so that shaking of the vial 12 travels the ball 50 within the vial 12 to inhibit drying of fluid against the sidewalls, clumping, and the like.

In one embodiment, the fluid delivery system 10 is configured for application of dental fluids, such as dental varnish, fluoride, and the like applied by dentists to teeth. In this regard, the system 10 may be provided as two pieces, namely, the fluid filled and sealed vial 12, and the applicator 16, both provided in a foil pouch. The dentist may open the foil pouch and then thread the applicator 16 onto the vial 12. The action of threading the applicator 16 onto the vial 12 dislodges the seal provided by the ball 50 and opens a channel for the varnish or other fluid to flow to the brush 40. Thin walls of the flexible portion of the vial 12 allow the user to squeeze to move the fluid to the brush 40.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:
1. A single use fluid delivery system, comprising:
a fluid containing vial fitted with a non-removable sealing plug;
a separate fluid applicator non-removably installable on the fluid vial; and
a ball seal structure located on the fluid vial and configured to seal the fluid vial until the applicator is installed,
wherein the fluid containing and sealed vial and the applicator are provided as separate pieces, and during use of the single use fluid delivery system the applicator is installed onto the vial, and during installation of the applicator onto the vial, the ball seal structure is dislodged and opens a channel for the fluid to flow to the applicator.

2. The system of claim 1, wherein the fluid contained in the vial comprises a dental treatment fluid.

3. The system of claim 1, wherein the vial includes a sidewall sufficiently thin so as to enable a user to squeeze the vial using hand pressure to urge the fluid toward the applicator during use of the fluid delivery system.

4. The system of claim 1, wherein one end of the vial includes an opening configured to cooperate with the sealing plug, and an opposite end that tapers to a seal section, wherein the seal section includes an enlarged docking port having internal threads.

5. The system of claim 4, wherein the opening of the vial configured to cooperate with the sealing plug includes an enlarged rim and the sealing plug includes rim locks that lock the sealing plug to the rim, wherein if the sealing plug is forcibly removed from the rim, the rim or the rim locks or both are sufficiently damaged so that the sealing plug is no longer suitable for sealing the vial.

6. The system of claim 4, wherein an end of the applicator includes threads to cooperate with the internal threads of the docking port of the vial.

7. The system of claim 6 wherein the end of the applicator having the threads also includes locking structure to lock the applicator to the vial when the applicator is threaded onto the vial.

8. The system of claim 1, wherein the vial includes a reservoir and a docking port each having a diameter and located on opposite sides of the ball seal structure, and the ball seal structure comprises a ball located within a throat of the ball seal structure, the throat having a reduced diameter as compared to the reservoir and the docking port, and a retaining ring, wherein the retaining ring cooperates with the ball to retain it in place in the ball seal structure and urge the ball against the throat when the applicator is not installed onto the vial.

9. The system of claim 8, wherein when the applicator is installed onto the vial, the ball is dislodged to break the seal provided by the ball to permit fluid to flow from the vial to the applicator.

10. The system of claim 9, wherein the applicator includes an inlet that cooperates with the ball to dislodge the ball during installation of the applicator onto the vial, the inlet configured to cooperate with the ball after installation of the applicator onto the vial such that the ball does not block the travel of fluid from the vial to the applicator.

11. The system of claim 10, wherein the inlet includes a sinusoidal curvature so that the ball can only touch a portion of the inlet at any time and cannot block fluid from entering the inlet.

12. The system of claim 1, wherein a distal end of the applicator comprises a brush.

13. The system of claim 12, wherein the applicator is of one piece molded plastic construction and the brush is molded unitarily with the applicator.

14. The system of claim 12, wherein the brush comprises 2-6 concentric circular rows of bristles.

15. The system of claim 12, where the brush comprises bristles having a triangular or four-sided cross section.

16. The system of claim 12, where the brush comprises bristles having a width at a base of 0.01 to 0.04 inches.

17. The system of claim 12, wherein the brush comprises bristles having a length of 0.2 to 0.7 inches.

18. A single use fluid delivery system, comprising:
a vial containing a fluid and the vial being formed to be squeezable under hand pressure for dispensing of fluid from the vial, the vial having one end including a ball seal structure configured to seal the fluid vial and including a ball; and
a separate fluid applicator installable onto the fluid vial, the applicator having an inlet that cooperates with the ball of the ball seal structure to dislodge the ball during installation of the applicator onto the vial to enable fluid to travel from the vial to the applicator after installation of the applicator onto the vial, the inlet configured to cooperate with the ball after installation of the applicator onto the vial such that the ball does not block the travel of fluid from the vial to the applicator.

* * * * *